(12) United States Patent
Lang et al.

(10) Patent No.: US 6,553,262 B1
(45) Date of Patent: Apr. 22, 2003

(54) ARRANGEMENT FOR PATIENT MONITORING

(75) Inventors: Bernhard Lang, Feucht (DE); Johannes Neudecker, Erlangen (DE); Armin Bolz, Weingarten (DE)

(73) Assignee: Biotronik Mess-und Therapiegerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/399,295

(22) Filed: Sep. 17, 1999

(30) Foreign Application Priority Data

Sep. 18, 1998 (DE) ......................................... 198 44 296

(51) Int. Cl.[7] .............................................. A61N 1/362
(52) U.S. Cl. ..................... 607/32; 128/903; 128/904; 607/60
(58) Field of Search ............................. 607/30–32, 60; 128/903, 904

(56) References Cited

U.S. PATENT DOCUMENTS

| | | | |
|---|---|---|---|
| 4,675,656 A | | 6/1987 | Narcisse |
| 4,958,645 A | * | 9/1990 | Cadell et al. ............... 600/484 |
| 5,204,670 A | | 4/1993 | Stinton |
| 5,508,708 A | * | 4/1996 | Ghosh et al. ............... 342/457 |
| 5,626,630 A | | 5/1997 | Markowitz et al. |
| 5,720,770 A | * | 2/1998 | Nappholz et al. ............. 607/30 |
| 5,782,878 A | | 7/1998 | Morgan et al. |
| 5,844,522 A | * | 12/1998 | Sheffer et al. ............... 342/457 |
| 5,959,529 A | * | 9/1999 | Kail, IV ..................... 340/539 |

FOREIGN PATENT DOCUMENTS

| | | |
|---|---|---|
| DE | 44 41 907 A1 | 6/1995 |
| DE | 197 58 393 | 7/1999 |
| GB | 2 285 135 A | 6/1995 |
| WO | WO 97/00708 | 1/1997 |

OTHER PUBLICATIONS

"Locating Lost Patients with Alzheimer's Disease", IEEE Communications Magazine, Apr. 1998, pp. 69–71, Fig. 3,5, p. 70 Li.Sp., Abs. 2.

* cited by examiner

*Primary Examiner*—George R. Evanisko
(74) *Attorney, Agent, or Firm*—Christie, Parker & Hale, LLP (57) ABSTRACT

An arrangement for patient monitoring. The arrangement includes at least one body sensor to detect a physiological parameter as body signal data and at least one of a body signal processing unit connected to the body sensor for processing body signal data, and a therapy device designed to act on the patient. In addition, the arrangement includes a monitoring center having a signal field strength evaluation means, a mobile phone terminal designed to transmit the data from at least one of the body signal processing unit and the therapy device to the monitoring center and from the monitoring center to the therapy device, and a cellular mobile phone network. The mobile phone terminal is operable in the cellular mobile phone network. The arrangement further includes a base station coordinate storage unit for storage of coordinate data and a mobile phone exchange linked to the base station coordinate storage unit for the reception of position data of the mobile phone terminal. The signal field strength evaluation means is utilized for evaluating signal field strength data reflecting the distance of the mobile phone terminal from at least one base station together with coordinate data of at least one active base station of the mobile phone network in order to determine the whereabouts of the patient.

11 Claims, 3 Drawing Sheets

ARRANGEMENT FOR PATIENT MONITORING

BACKGROUND OF THE INVENTION

In the event of serious health disorders or after major medical interventions, such as after a heart transplant, long-term uninterrupted monitoring of the patient's condition is indicated for early detection of a possible rejection reaction. With a view to the quality of life of the person affected, and also for reasons of capacity and costs, this should occur outside a clinic.

Also with individuals with implanted electronic medical devices, such as cardiac pacemakers, constant monitoring of the condition of the patient or of the device is often necessary and usually at least the capability of immediate signaling of life-threatening conditions of the patient or of the device, associated with simultaneous determination of the whereabouts of the patient, is desirable.

For various applications, there are a large number of known arrangements for outpatient monitoring.

U.S. Pat. No. 5,626,630 describes a medical telemetry system operating with an implantable quasi-passive transponder which includes, in addition to the transponder, a relay device to be worn on the body of the patient and a remote monitoring station.

German patent application P 197 58 393.8 of the applicant describes an arrangement for patient monitoring in which a patient device is activated automatically in response to a specific position of the patient for data transmission to a central monitoring center, in particular via a telephone network.

WO 97/00708 describes an advanced, very expensive system for worldwide patient positioning and for data transmission of implanted devices to suitable evaluation points. To determine the geographical position of patient based on the satellite navigation system GPS, the system includes a special receiver which the patient carries.

In the same expensive manner, the determination of patient location occurs in the cardiac stimulation system with expanded communication and monitoring capabilities according to U.S. Pat. No. 5,720,770, which moreover also provides for the use of the fixed telephone network or a mobile phone network for the transmission of relevant data.

BRIEF SUMMARY OF THE INVENTION

The object of the invention is to report a simple, economical arrangement for patient monitoring, in particular of individuals with implanted electronic medical devices, which enables an adequately accurate determination of the whereabouts of the patient in the event of an emergency.

The object is accomplished by means of an arrangement with the characteristics reported in claim 1.

The invention includes the underlying idea of using the position-relevant data constantly internally available in a cellular mobile phone network for position determination of the patient and to do without special means for geographic position determination.

This idea is based on the one hand on the fact that at the operating company of a mobile phone network, the geographic coordinates of all base stations used are present and each remote device addressed is, of course, located within the transmission and receiving range of at least one base station, but usually a plurality of base stations at the same time. On the exchange level of the mobile phone system, the information as to which base station is involved is also present, such that approximate locating of the patient is already possible on the basis of the base station position data.

Moreover, in a modem mobile phone system, to implement automatic handover between different base stations, among other things, measurements of the signal propagation time at least to the base station currently active for the terminal in question occur such that additional position-relevant information is present in the system with propagation time information. If the propagation times to a plurality of adjacent base stations are measured at the same time, it is possible to obtain a very precise determination of the location of the terminal in question and thus of the patient from their position data and the associated propagation time values. The propagation time data may, depending on the concrete organization of the network, be queried on the terminals or at the base stations and possibly also at the exchange level.

And finally, the fact that the base stations usually operate with directional antennas offers a capability for refined position determination of the patient by determining and evaluating which antenna of the base station the connection with the patient-terminal is made with.

Starting from these considerations, it is reasonable for the monitoring center of the patient care system to be connected for reception of position data of the mobile phone terminal (in addition to the connection with the patient terminal) with a mobile phone exchange or the center of the mobile phone network.

Position data evaluation means for evaluation of propagation time data reflecting the distance of the mobile phone terminal from at least one base station are allocated to the monitoring centers along with coordinate data of the active or reachable base station(s) of the mobile phone network—which includes the variant that these evaluation means lie within the response range of the mobile phone network operator and only the result data are feed into the patient monitoring system.

From the above basic ideas, it is clear that the simultaneous processing of propagation time data relative to a plurality of base stations is preferred. A determination of the signal propagation times to a plurality of base stations can, if not provided anyway in the standard protocol of the network used, be organized within the framework of a special protocol which is agreed to between the operator of the patient monitoring system and the operator of the mobile phone network. The evaluation by means of known trigonometric positioning procedures takes place most expediently at the patient monitoring center.

Another preferred embodiment consists in that the position determination unit has propagation time storage means to store the time variation of propagation time data over a prespecified period of time. Thus, it is possible to reconstruct a path of movement of the patient within the transmission range of the current base station (or plurality of base stations), which is helpful for accurate determination of the current position. For this, it may, in particular, be reasonable to select the time period to extend back far enough that earlier connections to other base stations are detected with reasonable probability.

Based on the above, another preferred embodiment consists of the position determination unit having means for detection of the antenna allocation upon connection of the mobile phone terminal with the active base station.

For the embodiment of the invention, expediently a well-designed GSM mobile phone network must be selected, according to current technology, in particular a D network or the E network. In the interest of the most gap-free patient monitoring globally possible, a connection of the patient monitoring system to all established mobile phone networks with a high degree of area coverage is particularly advantageous.

In order to keep the power requirement of the patient unit (of the mobile phone terminal) and thus the maintenance cost low and finally in order to also enable a high degree of miniaturization, activation should occur only as needed or in any case also for test purposes at relatively long intervals.

Consequently, advantageously, a parameter monitoring unit connected with the body signal processing unit or the therapy device to monitor the values of the physiological parameter or an operating parameter of the therapy device and switching means connected with the output of the parameter monitoring unit or activation of the mobile phone terminal in response to the detection of an abnormal value are provided. Moreover, manually or acoustically activated switching means for activation of the terminal by the patient himself may be provided.

A particularly useful application of the invention is found in the case of an implanted cardiac therapy device—such as a cardiac pacemaker for antibradycardiac or antitachycardiac stimulation of the heart or an automatic defibrillator or cardioverter—with a connected stimulation or shock electrode arrangement, with the body sensor and the downstream body signal processing unit designed to pick up and process heart signals for detection of cardiac arrhythmias, in particular life-threatening ones (e.g.: ventricular fibrillations or prestages thereof).

The body signal processing unit here includes, in particular a rate determination and evaluation unit for the determination and preferably also for retrospective evaluation of the heart rate as a physiological parameter and the parameter monitoring unit includes storage and comparison means to store at least one limit value based on the heart rate or its time variation and for comparison with this limit value for output of a control signal to the switching means when the limit value is exceeded.

Moreover, the parameter monitoring unit expediently includes detection, storage, and comparison means for the monitoring of at least the battery voltage and/or the impedance of the stimulation or shock electrode arrangement and/or the stimulation pulse amplitude for the output of a control signal to the switching means when the battery voltage or pulse amplitude falls below a limit value or when an electrode impedance limit value is exceeded.

The mobile phone terminal—which can moreover be a completely standard mobile phone with the provision of the above-discussed special means for emergency activation—has an interface device for connection with the body signal processing unit and/or the therapy device which includes encryption means for conversion of body signal or therapy device data into the data format of the mobile phone network.

BRIEF DESCRIPTION OF THE DRAWINGS

Advantageous improvements of the invention are also characterized in the dependent claims or are presented in detail in the following along with the description of the preferred embodiment of the invention with reference to the figures. They depict:

DETAILED DESCRIPTION OF THE INVENTION

Figure 1:
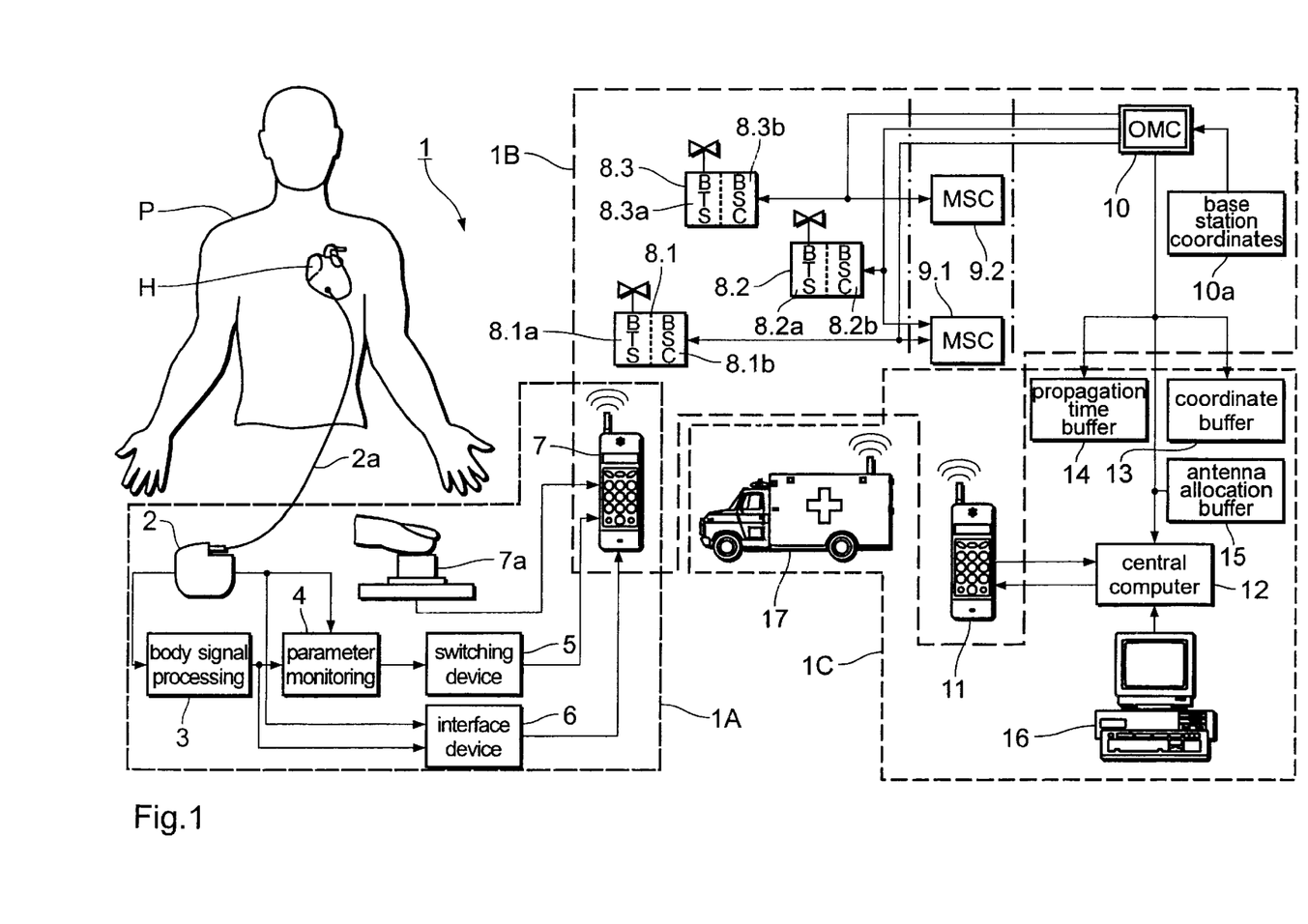
FIG. 1 a sketch reflecting the principle of a preferred embodiment of the entire arrangement, FIG. 2 a simplified functional block diagram of the patient-end components of a modified arrangement according to FIG. 1, and FIG. 3 a simplified functional block diagram of the means for position determination in another modified embodiment.

FIG. 1 depicts a patient monitoring arrangement 1 to monitor and determine the whereabouts of a pacemaker patient P.

The patient P has a cardiac pacemaker 2 with an electrode line 2a running to the heart H, which constitute the implanted portion of the arrangement 1. The electrode line 2a is also a sensor for cardiac activity and physiological parameters and the stimulation electrode. The implanted pacemaker 2 is connected via a prior art telemetry connection (not shown in the figure) with a body signal processing unit 3 and both directly and also—via a second data path—via the body signal processing unit with a parameter monitoring unit 4. A switching device 5 is located downstream from the output of the parameter monitoring unit 4. In addition, the pacemaker 2 and the body signal processing unit 3 are connected with an interface device 6. The interface device 6 is connected via a data link and the switching unit 6 [sic 5] via a control signal link with a mobile telephone 7. In addition, a manually activated ON-switch 7a is associated with this (which in practice will be an appropriate function key of the mobile phone itself). The aforementioned components form a patient unit 1A.

The mobile phone 7 is also an element of a GSM mobile phone network 1B, to which a plurality of base stations also belong, of which three adjacent base stations 8.1 through 8.3 are depicted in the figure. Each of these includes a base transceiver station (BTS) 8.1a, 8.2a, and 8.3a, respectively, as well as a base station controller (BSC) 8.1b, 8.2b, and 8.3b, respectively. On the level of the switching subsystem, in the example depicted, one and the same mobile switching center (MSC) 9.1 is associated with the base stations 8.1 and 8.2, and a different MSC is associated with the base station 8.3. An operation and maintenance center (OMC) 10 is associated with all three base stations 8.1 through 8.3. The distribution of functions among the BTS/PSC [sic BSC], the MSC, and the OMC is concretely defined in the respective system and needs no further general explanation here.

It is merely required here that a base station coordinate memory 10a in which the geographical position data of all base stations of the network 1B are stored be associated with the OMC 10, and that the OMC be designed for central recording of the measured propagation times and the detected diversity assignments in the base stations. And finally, a second mobile phone depicted in the figure, i.e., a terminal 11 associated with a patient monitoring center IC, also belongs to the network 1B.

The centerpiece of the patient monitoring center is a central computer 12, which is connected bidirectionally with the terminal 11 (which here symbolically represents a plurality of terminals essential in practice) and is also connected on the input side with the OMC 10. A coordinate buffer memory 13, a propagation time buffer memory 14 for the propagation time values measured, and an antenna allocation buffer memory 15 for the antenna allocations of the base station(s) detected relative to the terminal 7 and a plurality of PC workstations, for which again only one PC 16 is depicted, are allocated to the central computer 12. And finally, emergency resources, which are symbolized in the figure by the ambulance 17, are allocated to the patient monitoring center and can be brought into use via the mobile phone network 1B—not depicted in detail in the interest of clarity.

Figure 2:
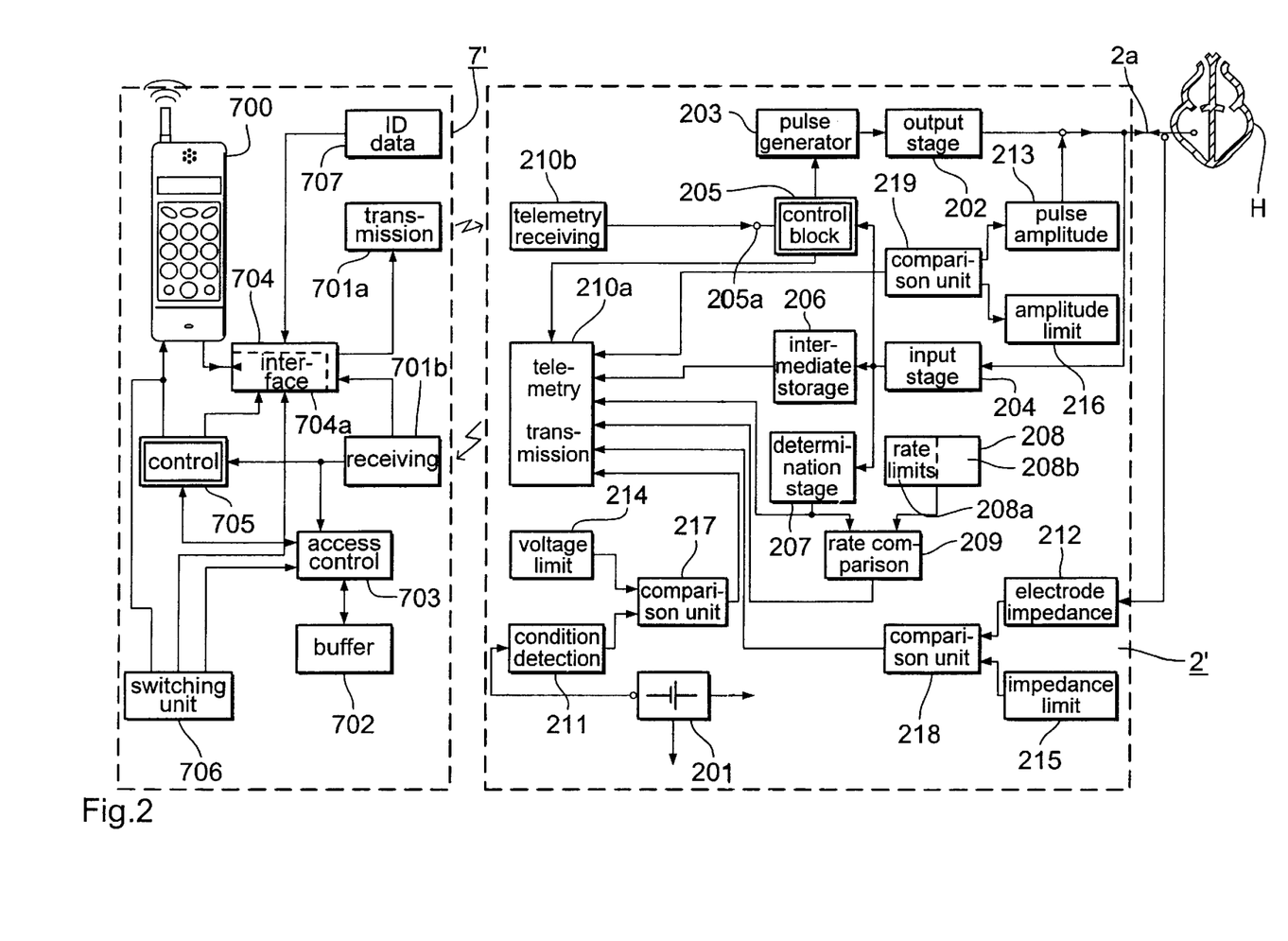

FIG. 2 is a simplified functional block diagram of the patient-end section 1A' of a patient monitoring arrangement modified relative to FIG. 1, which depicts only the functional components essential for the explanation of the embodiment of the invention. In contrast to the depiction of the principle in FIG. 1, the function units to be allocated to the body signal processing unit as well as the parameter monitoring unit are here integrated into the pacemaker itself.
p The cardiac pacemaker 2' otherwise has a largely known design and is of a type which enables at least ventricular stimulation as well as detection of ventricular cardiac signals. For this, it includes a battery 201 for power supply, a stimulation pulse generator 203 connected with the ventricular electrode 2a placed in the ventricle of the heart H via an output stage 202 on the output side as well as an input stage 204 connected with the electrode 2a on the input side. The pacemaker control functions are combined in the control block 205 in the figure, which has programming inputs 205a for external programming of the pulse rate and amplitude as well as for activation of additional functions, for example, tachycardia termination pulse sequences.

A heart signal intermediate storage 206 and a heart rate determination stage 207, in which the heart signals picked up (IEGM=intracardial electrograms) are temporarily stored and are also processed for the determination of the current heart rate, are connected downstream from the input stage 204 (in addition to the control block 205). Moreover, the pacemaker includes a rate limit value memory 208 with two storage zones 208a and 208b for a top and a bottom rate limit and a rate comparison unit 209 connected on the input side with the memory 208 and with the heart rate determination stage. Both the heart signal intermediate storage 206 and the heart rate determination stage 207 as well as the rate comparison unit 209 are connected on the output side with a pacemaker-side telemetry transmission unit 210a.

A battery condition detection unit 211 is associated in a known manner with the pacemaker battery 201 and an electrode impedance detection unit 212 and a pulse amplitude detection unit 213, both also already known, are associated with the output stage 202. In each case, limit value memories 214 for the battery voltage, 215 for the electrode impedance, and 216 for the pulse amplitude and in each case a comparison unit 217 through 219 are associated with or connected downstream from the detector units 211 through 213. The outputs of the comparison unit 217 through 219 are connected with the telemetry transmission unit 210a. A pacemaker-side telemetry receiving unit 210b is connected with the programming inputs 205a of the control block 205. The pacemaker-side telemetry units 210a, 210b are designed—like the external units (see below)—for long-range telemetry with a range of 1 to 2 meters.

An external patient device 7' includes a largely conventionally designed mobile phone 700 and a transmission and receiving unit 701a, 701b implementing a bidirectional telemetry path to the cardiac pacemaker (along with the implanted transmission and receiving unit 210b and 210a). It also includes a buffer storage 702 with storage access control 703 associated therewith for intermediate storage of data received via the telemetry link and an interface (possibly a PCMCIA card) 704, which has an encryption unit 704a for the connection with the mobile telephone portion 700 and for conversion of the data format of data to be transmitted to the patient monitoring center 1C (FIG. 1) and the programming data obtained therefrom supporting the transmission protocol of the respective mobile phone network.

And finally, the patient device includes a control stage 705 for automatic control of an emergency call, which is connected on the input side with the telemetry receiving unit 701b, on the output side with the telephone portion 700 and the interface 704 as well as with the memory access control 703 on the input and the output side. And finally, a manually activated emergency dialing switching unit 706 is provided to manually trigger an emergency call, which is also connected with the telephone portion, the memory access control, and the interface. An identification data memory 707 connected with the interface 704 includes invariable device and patient identification data.

In the following, the aspects of the operation of the embodiment according to FIGS. 1 through 3 relevant to the invention are explained; details of the pacemaker functions (including the telemetry function) as well as the data transfer in a mobile phone network are assumed to be known from the prior art. Also assumed is the fact that the mobile phone link has, in addition to the means for data transmission in the conventional manner, a voice channel.

In the continuous operation of the pacemaker 2 or 2', the heart rate is monitored permanently by the body signal processing unit 3 or—in the concrete example of the FIG. 2—by the heart rate determination stage 207, the rate limit value memory 208, and the rate comparison unit 209 as well as the function of the pacemaker by the parameter monitoring unit 4—according to FIG. 2 by the stages 211 through 219 concretely with regard to the battery voltage, pulse amplitude, and electrode impedance. If it is determined in the result of the limit value comparisons that a relevant measured value has departed from the admissible range, the mobile telephone 7 is activated directly by the switching device 5 in the embodiment according to FIG. 1 by the signal indicating the circumstance. The cycle includes the automatic turning on of the telephone, the dialing of a prestored emergency number (in an internal memory of the telephone portion, not separately depicted) and the transmission of a data string stored in the pacemaker 2 by the interface 6 after successful connection.

In the modified embodiment according to FIG. 2, the telemetry transmission unit 210a, which reflects an inadmissible value of one of the variables monitored, is activated automatically. This then transmits, under the control of the control block 205, an activation signal as well as a predefined (primary) data string, which includes specifically the IEGM read out of the cardiac signal storage 206 and the actual value of the heart rate available on the output of the heart rate determination stage 207 to the external patient device 7'.

There, the activation signal and the data string are received by the external telemetry receiving unit 701b and fed to the external control stage 705, and the primary data string is initially stored in the external buffer—under control of the control stage as well as the storage access control 703. After the mobile phone 700 is turned on and successful connection made with the terminal 11 of the patient monitoring center 1C called, the primary data string is read from the buffer and expanded with identification data from the identification data storage 707 to form a secondary data string, which is encrypted in the encryption unit 704a and forwarded to the patient monitoring center as an emergency call.

There, the emergency call is received by the mobile phone 11, and the data string is fed to the central computer 12 and transferred from it to a PC workstation 13, where an immediate evaluation for analysis of the emergency and for specification of immediate measures can be made by an on-duty cardiologist.

Parallel to the data evaluation, determination of the whereabouts of the emergency patient is carried out based on the message of his mobile telephone 7 or 700 to one or a plurality of the base stations 8.1 through 8.2 of the GSM network 1B as well as an evaluation of the signal propagation time and possibly antenna allocation data determined in the system. From the memory 10a in the OMC 10, the geographical data of the actively connected base station as well as those of its adjacent BTCs, relative to which signal propagation rime measured values are present, are read out into the coordinate buffer 13. The available propagation time data—possibly with its time variation over a predefined period of time—are transferred to the propagation time buffer 14. The data, which represent which of the directional antennas of the base station(s) through which the connection or the propagation Lime measurements occurred, are loaded into the antenna allocation buffer memory 15. Accessing the contents of this storage as well, the central computer 12 calculates the position of the mobile phone 7 of the emergency patient by using known navigation algorithms.

If the evaluation of the data transmitted has indicated the necessity of the use of an ambulance, the emergency resources 14 are provided with the indication of position and the evaluation result and can visit the patient.

Moreover, it is possible, if a pacemaker problem or perhaps a tachycardia incident which cannot be handled automatically by the pacemaker occurs, to undertake a programming intervention on the pacemaker via a the mobile phone link 11–7 as well as (in the embodiment according to FIG. 2) the bidirectional telemetry link 701a–210b, to terminate the threatening situation, perhaps without the use of an ambulance. In this connection, it is expedient to implement the arrangement with inquiry components in order to be able to check the success of the programming. Such components are known to the person skilled in the art and have consequently been omitted in the present example, in the interest of improved clarity.

The connection between the patient terminal and the monitoring center, once established, can be maintained in the case of an emergency until the emergency resources have reached the patient. This is indicated in particular if the position data indicate a continuing change in position—for example, because a patient (possibly in a motor vehicle) has not yet noticed a potentially dangerous pacemaker problem which has occurred and the activation of his mobile telephone or because he is on public transportation, which he is unable to stop. Otherwise, the connection may be interrupted again to save capacity and cost after dispatching of the emergency resources by the monitoring center. In any event, in this case of position tracking (possibly over a relatively long period), the use of adequately dimensioned buffers 13, 14, preferably organized on the FIFO principal, is reasonable.

Figure 3:
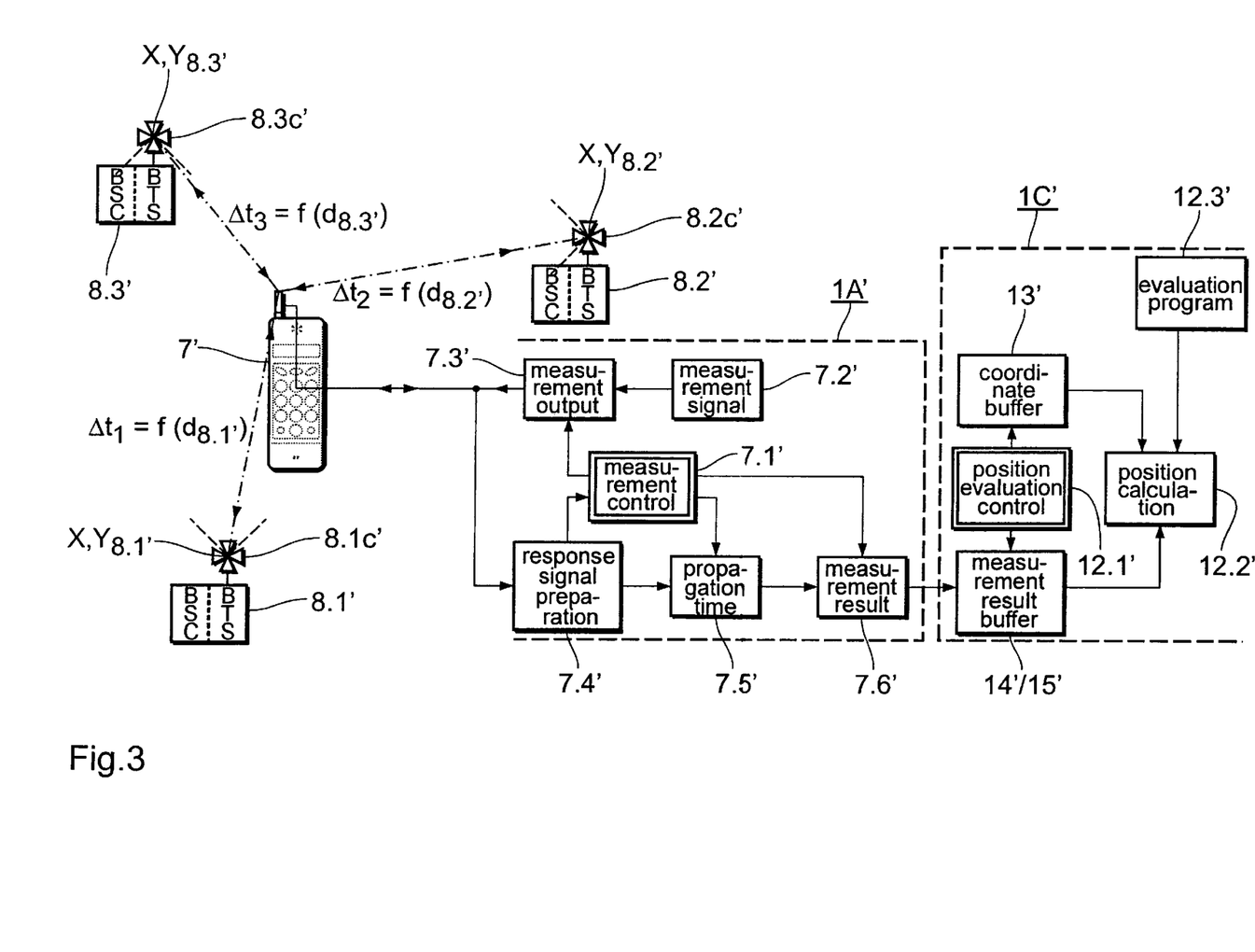

FIG. 3 is a detailed depiction (again as a simplified functional block diagram) of the means for position determination in an embodiment modified relative to FIG. 1. The reference characters of components already depicted in FIG. 1 are repeated. The modification consists primarily in that the patient device 1A' is designed for execution of propagation time measurements relative to a plurality of base stations 8.1' through 8.3' and for transmission of the propagation time data to the patient monitoring center 1C'.

For this, the patient device 1A' includes a measurement control unit 7.1', a measurement signal generator 7.2', a measurement output unit 7.3' connected via a control input with a measurement control unit 7.1', a response signal preparation unit 7.4', a propagation time calculation unit 7.5' connected therewith on the input side and via a control input with the measurement control unit 7.1', and a measurement result memory 7.6' connected with its output as well as with the measurement control unit 7.1'.

Upon activation of the patient device (see above in this regard) the measurement control unit 7.1' feeds propagation time measurements according to the operating protocol agreed to and according to a stored program to the reachable base stations 8.1' through 8.3', which are at distances of $d_{8.1'}$, $d_{8.2'}$ or $d_{8.3'}$ from the patient device. Thus, a measurement and inquiry pulse sequence is prepared in each case by the measurement signal generator 7.2' and transferred by the measurement output unit 7.3' under the control of the measurement control unit 7.1' to the transmitting portion (not shown) of the mobile phone 7'. The response signals of the reachable base stations received by its receiving portion (also not shown) include, according to the protocol in each case, a return signal and a station and antenna identification of the receiving antenna of the respective antenna group of 8.1 c', 8.2c', or 8.3c' and arrive at the response signal preparation unit 7.4', where the measurement signal component is separated and sent to the propagation time calculation unit 7.5', while the identification string is delivered to the measurement control unit 7.1'. The propagation times $\Delta t_1 = f(d_{8.1'})$, $\Delta t_2 = f(d_{8.2'})$, and $\Delta t_3 = f(d_{8.3'})$ calculated in the stage 7.5' are finally stored allocate associated station and antenna identification in the measurement result memory 7.6'.

The patient monitoring center 1C' has a coordinate buffer 13' and a measurement result buffer 14'/15', which is supplied here with the presence of measurement results from the measurement result memory 7.6' of the patient device 1A'. A position evaluation controller 12.1' accesses the memories 13' and 14'/15' and initiates a position calculation in a calculation unit 12.2' according to known trigonometric procedures, whose algorithm is stored in an evaluation program memory 12.3'.

Here, in the presence of propagation time values to a plurality of base stations, the distances thereto are determined from the propagation times, using the geographical positioning data of the base stations of the geographic location of the terminal 7' at the time of the measurement. If there are fewer than three propagation time values, to increase the accuracy of the position determination, the stored antenna allocation data, which indicate the angular range of the respective base station in which the patient device is located, are also included in the evaluation.

In a more expensive embodiment, the measurement control unit 7.1' of the patient terminal as well as the measurement result buffer 14'/15', the position evaluation controller 12.1', and the calculation unit 12.2' of the center are designed for execution or evaluation of a plurality of measurements over a predefined period of time to determine the path of movement of the patient device, which enables a positional prediction at a future point in time. With such an embodiment, use of emergency resources is enabled even for the aforementioned rare cases in which the patient is not in a fixed location in the event of an emergency.

The invention is not restricted in its execution to the above explained preferred exemplary embodiments. Rather, a large number of variants is conceivable, which make use of the solution depicted in otherwise designed embodiments.

The arrangement described by way of example, wherein an evaluation of the signal propagation times occurs, can be designed with substantially the same structure for the evaluation of the signal field strength in the mobile phone network. The evaluation means are then preferably designed for detection and evaluation of the bit error ratios (dependent on the signal field strength of the respective base station).

The patient device can, in particular also be implemented as a defibrillator or a cardioverter or a medication infusion pump.

In an arrangement serving exclusively to monitor the condition of a patient without an active therapy function, a unidirectional transmission link may be completely adequate to transmit the relevant body data from the device, instead of a bidirectional telemetry link.

Instead of "classical" telemetry, even other short range transmission processes may in principle be used, whereby it is, of course, necessary to ensure low energy consumption for the implanted portion.

The aforementioned functional components may be implemented according to the current standards and transmission protocols as hardware or software elements and can be combined or integrated functionally in a modified manner.

The voice channel assumed in the above explanation may possibly even be omitted in a simplified and extensively miniaturized embodiment of the arrangement.

On the patient device, in particular on the mobile radio terminal itself, alarm means and/or a display of relevant condition information may be provided for the patient, to adequately inform him of the dangerous problem which has occurred, such that he possibly can participate in the solution—perhaps by immediately taking specific medication or visiting a nearby clinic. A converter which converts a predefined section of the telemetry data string, at least the section characterizing the origin of the activation signal, into textual information serves to implement such a display.

What is claimed is:

1. Arrangement for patient monitoring, comprising:
    at least one body sensor to detect a physiological parameter as body signal data;
    at least one of a body signal processing unit connected to the body sensor for processing body signal data and a therapy device designed to act on the patient;
    a monitoring center having a propagation time evaluation means;
    a mobile phone terminal designed to transmit the data from at least one of the body signal processing unit and the therapy device to the monitoring center and from the monitoring center to the therapy device;
    a cellular mobile phone network having a plurality of ground base stations and having an operating protocol, the mobile phone terminal being operable in the cellular mobile phone network;
    a base station coordinate storage unit for storage of coordinate data;
    a least one of a mobile phone exchange and a center of the mobile phone network linked to the monitoring center for the reception of position data of the mobile phone terminal by the monitoring center;
    antenna allocation storage means for storage of antenna allocation data upon connection of the mobile phone terminal with an active base station;
    wherein the base station coordinate storage unit is connected to the propagation time evaluation means;
    wherein the position data for the mobile phone terminal comprise propagation time data;
    wherein the propagation time evaluation means is utilized for evaluating said propagation time data reflecting the distance of the mobile phone terminal from at least one base station together with coordinate data of at least one active base station of the mobile phone network in order to determine the whereabouts of the patient; and
    wherein the antenna allocation storage means is connected to the propagation time evaluation means and is designed for the evaluation of stored antenna allocation data with priority secondary to propagation time data.

2. Arrangement according to claim 1, wherein the propagation time data evaluation means is designed for evaluation of coordinate data of a plurality of adjacent base stations based on the operating protocol of the mobile phone network providing multiple propagation time measurement.

3. Arrangement according to claim 1, characterized in that the storage means for storage of the propagation time is connected to the propagation time data evaluation means.

4. Arrangement according to claim 1, characterized in that the mobile phone network is a GSM network.

5. Arrangement according to claim 1, further comprising a parameter monitoring unit and a control means, the body signal data measured by the body signal processing unit having at least one physiological parameter with measurable values and the therapy device having at least one operational parameter, wherein the parameter monitoring unit and the body signal processing unit monitors the measured values of the physiological parameter and/or the operational parameter of the therapy device and wherein the control means is connected with the output of the parameter monitoring unit for activation of the mobile phone terminal and dialing of a preprogrammed call number in response to detection of an abnormal value of the physiological parameter measured by the body signal processing unit or of the operational parameter of the therapy device.

6. Arrangement according to claim 5, wherein the body signal processing unit has a rate determination and evaluation unit for the determination and evaluation of the heart rate as the physiological parameter and the parameter monitoring unit comprises storage and comparison means for storage of at least one limit value related to the heart rate or the heart rate's time variation and for comparison of the heart rate with the limit value, wherein a control signal is outputted to the control means when the limit value is exceeded.

7. Arrangement according to claim 6, wherein the rate determination and evaluation unit of the body signal processing unit retrospectively evaluates of the heart rate.

8. Arrangement according to claim 1, wherein the therapy device is an implantable cardiac therapy device with a stimulation or shock electrode arrangement connected thereto, and the body sensor and the body signal processing unit are designed to pick up and process cardiac signals for detection of a cardiac arrhythmia, and the parameter moinitoring unit further comprises detection, storage, and comparison means for the monitoring of at least one of a battery voltage and/or an impedance of The stimulation or shock electrode arrangement and/or a stimulation pulse amplitude for the output of a control signal to the control means when the battery voltage drops below a limit value or when the electrode impedance exceeds a limit value.

9. Arrangement according to claim 1, characterized by manually activated switching means for activation of the mobile phone terminal and dialing of a preprogrammed call number.

10. Arrangement according claim 1, wherein the therapy device is an implantable cardiac therapy device with a stimulation or shock electrode arrangement connected thereto, and the body sensor and the body signal processing unit are designed to pick up and process cardiac signals for detection of a cardiac arrhythmia.

11. Arrangement according to claim 1, further comprising an interface device for connection with the body signal processing unit and/or the therapy device, and wherein the mobile phone network has a data format and the interface device is allocated to the mobile phone terminal, which has encryption means to convert the body signal data or the therapy device data into the data format of the mobile phone network.

* * * * *

UNITED STATES PATENT AND TRADEMARK OFFICE
CERTIFICATE OF CORRECTION

PATENT NO. : 6,553,262 B1 Page 1 of 1
DATED : April 22, 2003
INVENTOR(S) : Bernhard Lang et al.

It is certified that error appears in the above-identified patent and that said Letters Patent is hereby corrected as shown below:

Column 9,
Line 57, replace "a least" with -- at least --.

Column 10,
Line 49, replace "claim 1" with -- claim 5 --.
Line 57, replace "The" with -- the --.

Signed and Sealed this

Twenty-seventh Day of April, 2004

JON W. DUDAS
*Acting Director of the United States Patent and Trademark Office*